(12) United States Patent
Verboven et al.

(10) Patent No.: US 8,289,621 B2
(45) Date of Patent: Oct. 16, 2012

(54) REFLECTED DARK FIELD METHOD AND APPARATUS

(75) Inventors: Marc Verboven, Vloeiende (BE); Troy Blodgett, Flagstaff, AZ (US)

(73) Assignee: Gemological Institute of America, Inc., Carlsbad, CA (US)

( * ) Notice: Subject to any disclaimer, the term of this patent is extended or adjusted under 35 U.S.C. 154(b) by 816 days.

(21) Appl. No.: 12/287,188

(22) Filed: Oct. 7, 2008

(65) Prior Publication Data

US 2010/0085635 A1   Apr. 8, 2010

(51) Int. Cl.
*G02B 21/06* (2006.01)
(52) U.S. Cl. .......................................... 359/385; 356/30
(58) Field of Classification Search .................. 359/385; 356/30
See application file for complete search history.

(56) References Cited

U.S. PATENT DOCUMENTS

| | | | |
|---|---|---|---|
| 6,473,164 B1 * | 10/2002 | De Jong et al. | 356/30 |
| 2005/0213077 A1 * | 9/2005 | Sasian et al. | 356/30 |

* cited by examiner

*Primary Examiner* — Frank Font
(74) *Attorney, Agent, or Firm* — DLA Piper LLP (US)

(57) ABSTRACT

A reflected dark field structure includes a bottom plate, a support tube, a light unit, a diffuser structure, and a reflector unit that provides reflected dark field illumination, such that a gem held by the support tube and surrounded by the diffuser structure is illuminated and viewable through an aperture in the reflector unit. A method for imaging and analyzing a gem includes placing the gem onto a support tube where it is illuminated with dark field and reflected dark field illumination, and viewing the gem via an aperture located on a top reflector unit, which provides a top cover for the gem. Furthermore, a method and apparatus for obtaining images of a gem includes a dark field stage, a reflector unit, and an image-acquiring device, such that a gem placed in the dark field stage is illuminated, and such that the reflector unit covers the dark field stage and provides reflected dark field illumination, and such that the image-acquiring device is directed towards an aperture in the reflector unit.

9 Claims, 10 Drawing Sheets

REFLECTED DARK FIELD METHOD AND APPARATUS

TECHNICAL FIELD

The present invention is directed generally towards analyzing a gem, and more specifically towards a method and apparatus which provides illumination that improves the detail to which a gem may be observed.

BACKGROUND OF THE TECHNOLOGY

Today, vision analysis has a growing impact on production, production control, and quality control issues within many industries. The Diamond and Gem industry is no exception which has adopted digital imaging and vision analysis technology to improve the efficiency of manufacturing processes and improve the quality controlling stations. Examples are the high tech computer measuring devices that have taken over proportion measuring from the classic Proportionscope by the Gemological Institute of America, assignee of the subject application. Powerful computers and high resolution digital images are now available and have triggered the development of more highly sophisticated vision analysis tools and advanced vision analysis software programs.

The theoretical and practical knowledge in the vision industry is vast, but applying these optical tools and vision analysis knowledge to diamond clarity grading is rather new. There are many considerations in capturing a suitable clarity image such as lighting and the cost of hardware. Some of these considerations even involve compromises with how else the image can be used. A detailed image of only the grade setting inclusion may be useful for grading clarity, but capturing the whole diamond allows for a broader range of applications such as placing a more attractive image on a report or capturing symmetry faults. Capturing the whole image is also critical for determining the relative size of the inclusion.

Lighting is a particularly critical issue for the vision analysis of gems. Namely, the lighting must be sufficiently intense for photographing purposes, but must also be directed in a manner that minimizes direct (bright) reflections off crown facets which tend to make images unsuitable for clarity grading. Accordingly, there is currently a need for a method and apparatus for creating "technically correct" images that are also aesthetically lively.

SUMMARY OF THE INVENTION

The present invention addresses the aforementioned problems by providing an improved method and apparatus for providing illumination useful for analyzing a gem.

In accordance with the present invention, a dark field illumination apparatus is provided which provides a reflected illumination component.

An embodiment of the present invention provides a dark field illumination apparatus which includes a base plate, and a support tube positioned on the base plate and having an end configured to support a gem. A diffuser structure is configured to substantially encircle a gem supported by the support tube. A reflector unit is provided which has a reflecting surface positionable over the diffuser structure and to be opposite the surface of the base plate so that a gem supported by the support tube is substantially surrounded by the reflecting surface, the diffuser structure and the base plate. The reflector unit includes an aperture formed in the reflecting surface to allow a gem supported by the support tube to be viewed. A light unit is positioned to illuminate a gem supported by the support tube and so that a gem supported by the support tube is located between the light unit and the reflecting surface.

Another embodiment of the present invention includes a bottom plate, a support tube, a light unit, a diffuser glass, and a top reflector unit. Within such embodiment, the support tube is coupled substantially perpendicular to the bottom plate and configured to hold a gem which is to be illuminated by the light unit. A diffuser glass is coupled to the bottom plate and positioned so as to substantially surround a gem held by the support tube. A top reflector unit is also provided, which is coupled to the diffuser glass and substantially parallel to the bottom plate so as to substantially cover a gem held by the support tube. For this embodiment, the top reflector unit includes an aperture configured so as to allow a gem held by the support tube to be viewed.

In another embodiment, a reflected dark field apparatus is provided which includes a support tube affixed onto a base unit and configured to hold a gem. Within such embodiment, a light unit is positioned with respect to the base unit and configured to illuminate a gem held by the support tube. A diffuser glass structure is also provided and positioned so as to provide a perimeter around a gem held by the support tube. And finally, a top reflector unit having an aperture is positioned substantially perpendicular to the diffuser glass structure and substantially parallel to the base unit so as to provide a top cover for a gem held by the support tube, and configured so as to allow a gem held by the support tube to be viewed through the aperture.

In a further embodiment of the present invention, a method for analyzing a gem is also provided which includes the steps of placing the gem onto a support tube affixed to a base unit, and viewing the gem via an aperture located on a top reflector unit. Within such embodiment, the gem is illuminated by a light unit, and a diffuser glass structure is coupled to the base unit so as to provide a perimeter around the gem. Also, the top reflector unit is positioned substantially perpendicular to the diffuser glass and substantially parallel to the base unit so as to provide a top cover for the gem and a reflecting surface by which a reflected illumination component is provided.

In another embodiment of the present invention, an apparatus for obtaining images of a gem is provided which includes a dark field stage, a reflector unit, and an image-acquiring device. Within such embodiment, a gem placed on a support tube in the dark field stage is illuminated by a light unit. Also within such embodiment, the reflector unit substantially covers the dark field stage and further includes an aperture, wherein the imaging component of the image-acquiring device is directed substantially towards the center of the aperture.

In yet a further embodiment of the present invention, a method for obtaining images of a gem is provided. This method includes illuminating a gem placed on a support tube in a dark field stage, and positioning a reflector unit so that the gem is located between the reflector unit and the illumination source. The method also includes pointing an image-acquiring device substantially towards the center of an aperture in the reflector unit through which the gem may be imaged.

As will be appreciated upon consideration of the following detailed description of the invention and accompanying drawings, there are many advantages and features of the present invention, which in turn lead to many new and useful applications of the invention.

DETAILED DESCRIPTION OF THE INVENTION

The present invention is directed towards providing an improved method and apparatus for analyzing gems in a dark field by the use of dark field illumination and reflected dark field illumination.

Analyzing the clarity characteristics of stones via dark field illumination under a microscope is considered by the inventors of the subject application to be the best method for examining inclusions, given the level of reflections which can be produced from certain facets of a gem such as the crown facets of a diamond. Such analysis has included the use of digital photographs. However, to make the digital photographs more useful for a variety of other applications, a "reflected dark field" illumination set-up is provided by the present invention, which has been found to add more sparkle and life to the stone image, relative to traditional dark field illumination. Moreover, this reflected dark field set up minimizes direct reflections off crown facets that otherwise can interfere with the analyzing of a grade setting inclusion.

Figure 1:
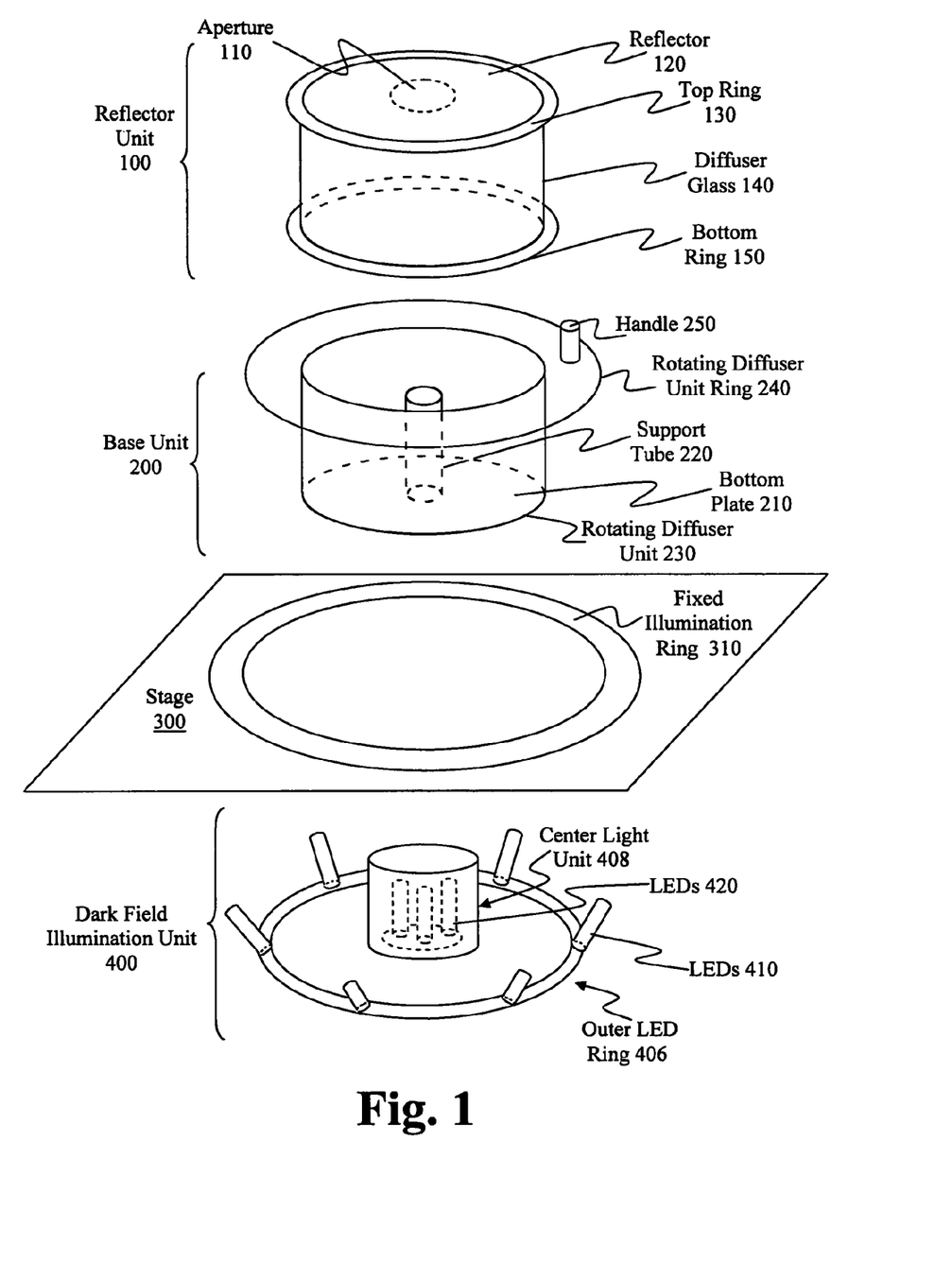
FIG. 1 is an exemplary reflected dark field apparatus according to an embodiment of the invention.

In FIG. 1, an exemplary reflected dark field apparatus according to an embodiment of the invention is provided. As illustrated, a reflector unit 100 is coupled with base unit 200 supported by stage 300. Illumination is provided from below the stage by dark field illumination unit 400. Within such embodiment, reflector unit 100 preferably includes aperture 110 formed in reflector 120, top ring 130, diffuser glass 140, and bottom ring 150.

Base unit 200 preferably includes bottom plate 210 and support tube 220, which are supported within a rotating diffuser unit 230. Rotating diffuser unit 230 includes a rotating diffuser unit ring 240 by which rotating diffuser unit 230 is supported on stage 300. Preferably, rotating diffuser unit ring 240 includes a handle 250 and is rotatably supported on fixed illumination ring 310, which in turn is supported in an opening 320 in stage 300, so that a user may rotate rotating diffuser unit 230 about the vertical axis of support tube 220 using handle 250.

Figure 2:
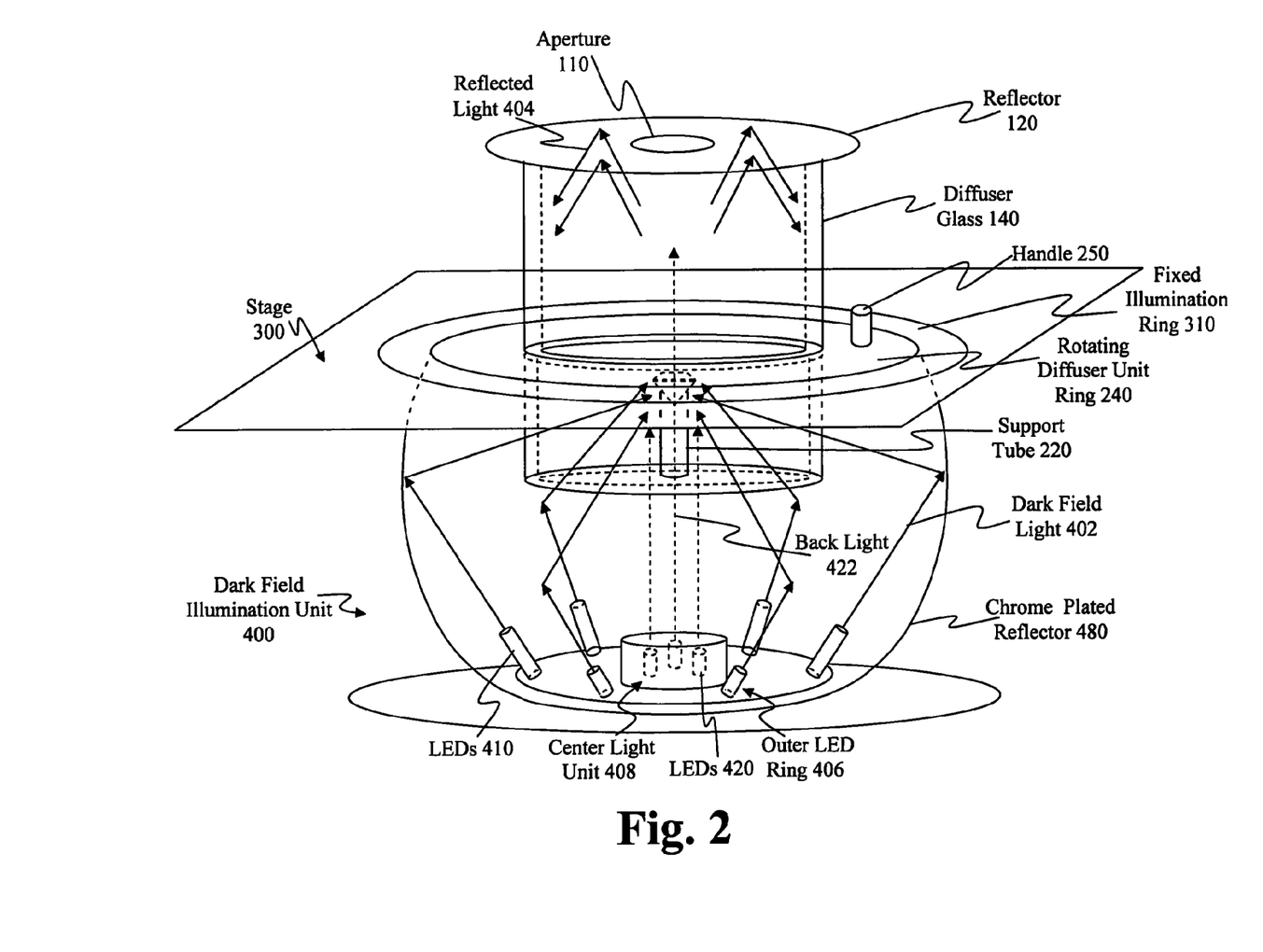
FIG. 2 is a light ray schematic of a reflected dark field apparatus according to an embodiment of the invention.

Illumination unit 400 preferably includes LEDs 410 in an outer LED ring 406, and LEDs 420 in a center light unit 408. Also included is a conventional dome shaped chrome plated reflector 480 (FIG. 2) which reflects light from the LEDs 410 in outer LED ring 406 toward the rotating diffuser unit 230 and support tube 220. The effect of the arrangement of base unit 200, stage 300 and illumination unit 400, is that support tube 220 is positioned below the upper surface of stage 300 and within the volume of chrome plated reflector 480, as illustrated in FIG. 2. Illumination unit 400 preferably includes a cylindrical housing or pot (now shown) in which the outer LED ring 406, the center light unit 408, and the chrome plated reflector 480 are contained and supported with respect to stage 300. Fixed illumination ring 310 preferably supports the chrome plated reflector 480 from above.

Rotating diffuser unit 230, bottom plate 210 and stage 300 are configured to permit the passage of light from illumination unit 400 into the space enclosed by the rotating diffuser unit 230 and reflector unit 100. Light transmissive materials may be employed, such as TEFLON® for bottom plate 210, and such as frosted boron silicate glass for the rotating diffuser unit 230, for such purpose. When reflector unit 100 is positioned over base unit 200, diffuser glass 140 and the walls of rotating diffuser unit 230 provide an embodiment of a diffuser structure which encircles a gem positioned on support tube 220.

In FIG. 2, a light ray schematic is provided to illustrate how the present invention minimizes direct reflections off crown facets of a gem being viewed, and provides reflected dark field illumination. In an exemplary embodiment, a diamond is placed in support tube 220 in a crown up position in the center of the illumination set up, preferably without the use of metal clamps. Outer LED ring 406 provides dark field light 402 to the diamond within rotating diffuser unit 230, and the space enclosed within reflector unit 100. The dark field light 402 from the LEDs 410 in outer LED ring 406 is reflected off of chrome plated reflector 480 so as to be incident on rotating diffuser unit 230 and bottom plate 210 of base unit 200. Preferably, the largest part of light reflected off of chrome plated reflector 480 which enters rotating diffuser unit 230 is directed through the diffuser glass of rotating diffuser unit 230 and straight to the pavilion of the diamond on the support tube. A portion of the reflected light is returned into the reflector through the bottom plate 210 of the diamond support tube holder. After passing through the frosted glass material of rotating diffuser unit 230 and the TEFLON® bottom plate 210 of base unit 200, the dark field light 402 illuminates the diamond, as well as enters reflector unit 100 where it reflects off reflector 120 as reflected light 404, as shown. To avoid an excessively dark center near the culet, support tube 220 is hollow and allows backlight 422 from LEDs 420 within center light unit 408, below, to pass directly through the support tube 220 and into the pavilion side of the diamond. In a preferred embodiment, the height of support tube 220 is also large enough so that the background is outside of the field of view of a camera or imaging device which is imaging the diamond through aperture 110. This avoids dust from the background from being picked up by the camera or imaging device. Most of the light going through the bottom plate 210 of the diamond support tube 220 into rotating diffuser unit 230 comes from the vertical LEDs 420 of the center light unit 408.

The reflected dark field set-up has been found to add sparkle to the traditional dark field images, and to keep hindering reflections to a minimum. The reflected dark field set-up has been found to achieve an increased light intensity level which allows for faster shutter speeds and more ideal exposure settings when imaging gems. While LEDs are a preferred light source, a halogen light source may be used with color temperature output corrected with a transparent blue daylight color temperature filter.

A neutral grey image background may also be created by forming bottom plate 210 of a TEFLON® material and combining a neutral density filter.

It should be appreciated that the reflected dark field set-up described above may be implemented in various ways. In one embodiment, for example, dark field illumination unit 400 is integrated into the base of a microscope. The design of stage 300 may also vary so as to allow for a gem to be analyzed from different angles or positions, such as where stage 300 includes a tilt and/or XYZ adjustment mechanism. With a mechanical X, Y, Z stage, the position of the stage can be adjusted in the X and Y and Z directions to keep the diamond centered in the image field of an imaging or viewing device. Another embodiment of a reflected dark field set-up will be described in connection with FIGS. 4A and 4B.

Figure 3A:
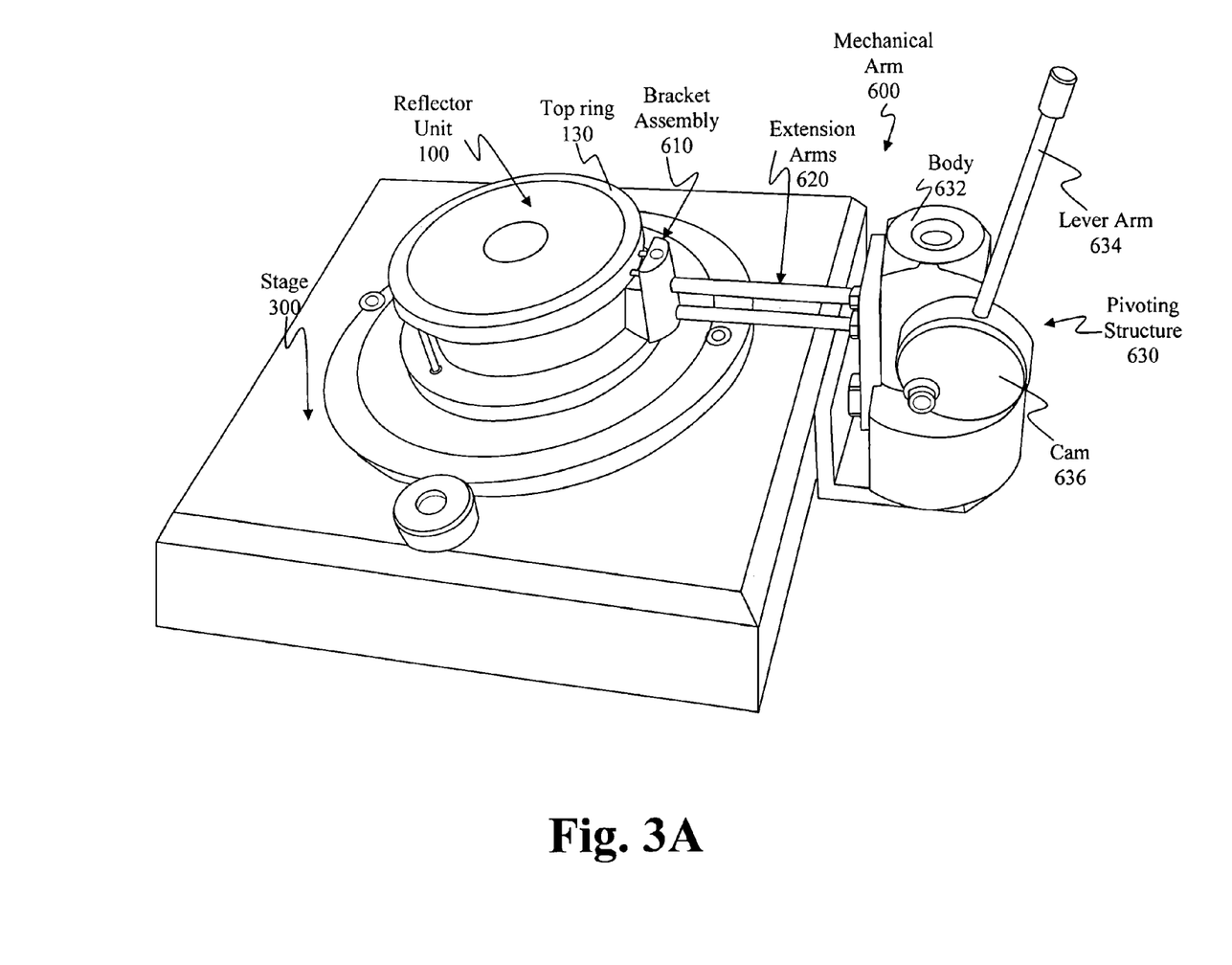
FIG. 3A is a schematic of a mechanical arm attached to the reflector unit according to an embodiment of the invention.

In another aspect of the present invention, the reflected dark field apparatus is further improved by adding a fine mechanical arm that enables the operator to remove/replace the "reflected dark field reflector setup" in a more automated and faster way. In FIG. 3A, an exemplary schematic of such a mechanical arm 600 is provided. Mechanical arm 600 includes a bracket assembly 610, extension arms 620, and a pivoting structure 630. Bracket assembly 610 is coupled to reflector unit 100.

In FIG. 3A a flange of top ring 130 of reflector unit 100 is shown supported by bracket assembly 610, and connected to bracket assembly 610 by way of two fasteners, as shown. Bottom ring 150 is also coupled to bracket assembly 610. Extension arms 620 couple bracket assembly 610 to a body portion 632 of pivoting structure 630. Lever arm 634 operates a cam-like structure 636 which pivots body portion 632 and causes extension arms 620 to lift bracket assembly 610 and reflector unit 100 (including top ring 130 and reflector 120, diffuser glass 140 and bottom ring 150) upwards and away from stage 300. The mechanical arm 600 lifts the dark field reflector unit 100 and can then swing the reflector unit 100 out of the way while a diamond is placed in the holder. The mechanical arm 600 provides a limited range of motion of the reflector unit, so that the camera lens and other parts of the device are protected from accidental contact with the reflector.

Figure 3B:
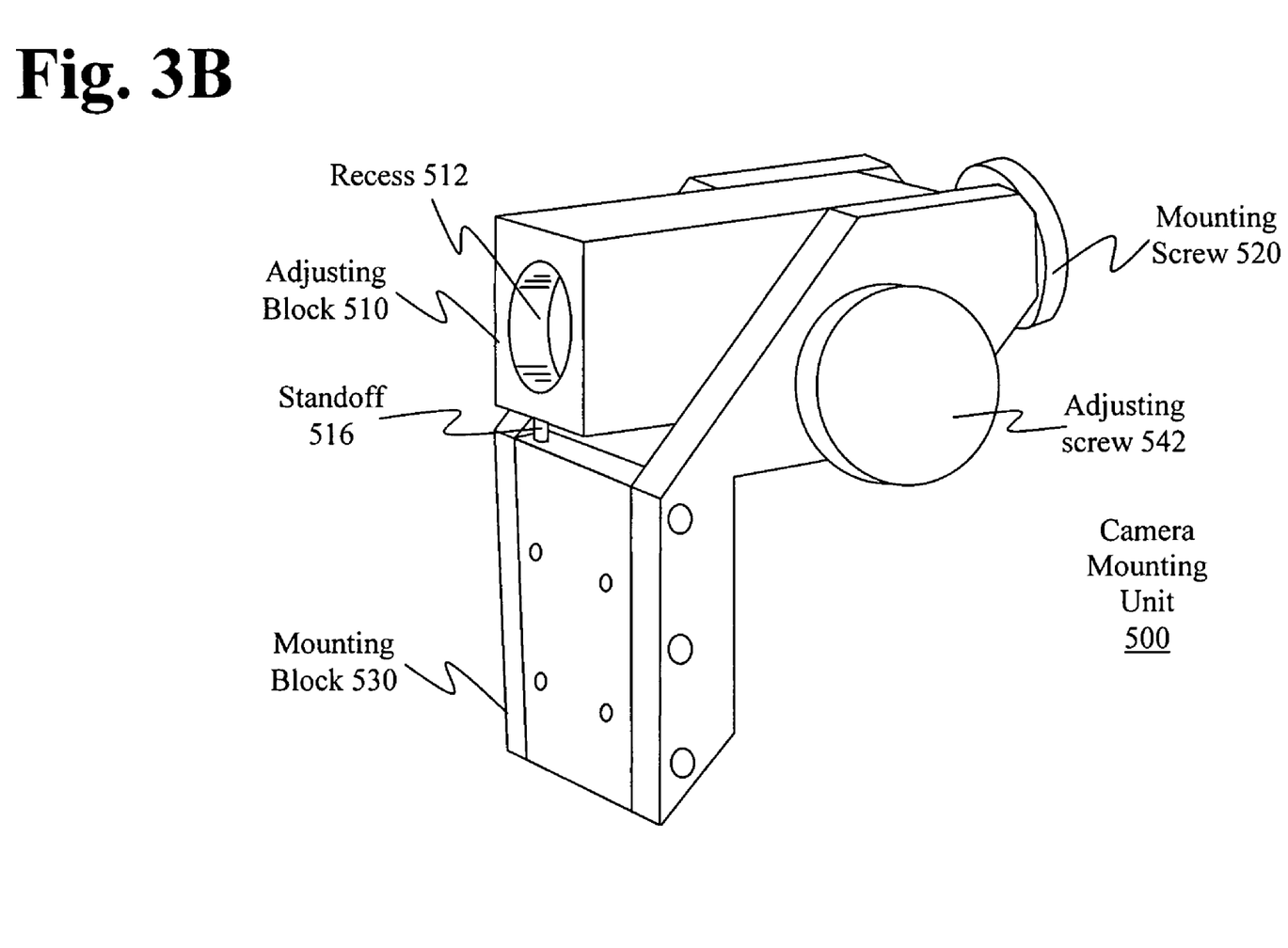
FIG. 3B is a schematic of a camera mounting unit according to an embodiment of the invention which uses a moveable stage.

The present invention has particular utility for photographing gems. Camera mounting units are described which permit a camera or other imaging device to be mounted to a microscope frame and oriented in a suitable manner to the reflected dark field apparatus in accordance with the present invention. An embodiment of such mounting unit when a moveable stage is employed, is illustrated in FIG. 3B. Preferably the camera mounting unit 500 includes adjusting block 510, mounting screw 520, and mounting block 530. Details of the camera mounting unit 500 are provided hereafter in connection with the description of FIGS. 8A-8C. During use, camera mounting unit 500 allows a camera lens axis to remain in the center of a microscope's illumination set-up which allows for shooting images through aperture 110 in reflector 120. The mounting unit 500 also secures the camera so as to extinguish disturbing vibrations caused by the movement of the shutter release which can result in a blurry image (often associated with close up or low light photography).

Figure 4A:
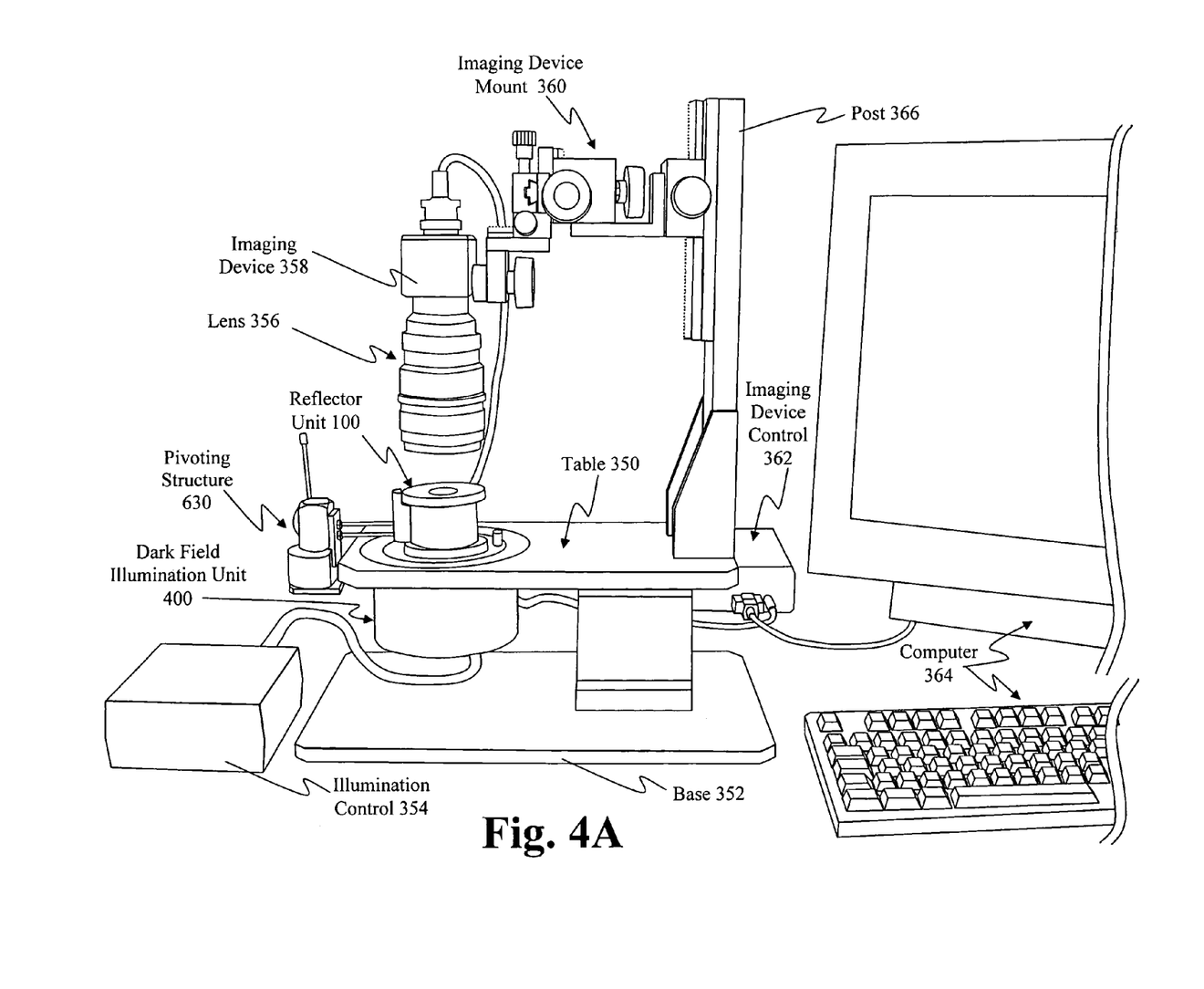
FIG. 4A is a simplified illustration of an embodiment of the reflected dark field apparatus supported by a table in relation to a positionable imaging device, as a part of an image capturing system suitable for use in gem clarity grading.
Figure 4B:
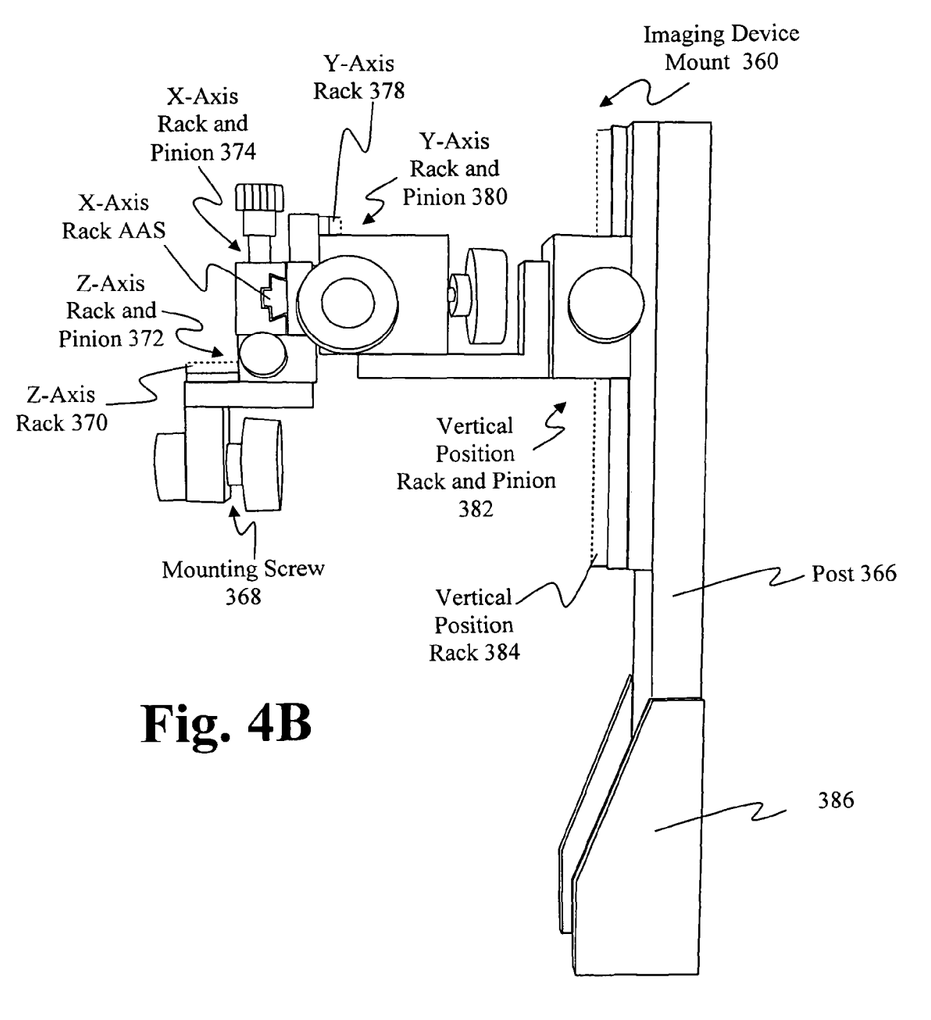
FIG. 4B is a enlargement the X-Y-Z moving stage and linear translation stage for positioning the imaging device relative to the reflected dark field apparatus in accordance with the embodiment of FIG. 4A.

Another embodiment of a reflected dark field imaging configuration is illustrated with FIGS. 4A and 4B in which a fixed table and moveable imaging device are employed. In FIG. 4A it can be seen that a table 350 is supported above a base 352. Dark field illumination unit 400, as previously described in connection with FIGS. 1 and 2, is coupled to and positioned below table 350. Illumination control 354 is provided by which the light sources within dark field illumination unit 400 are controlled. Included are switches and intensity controls by which the output of various combinations of the LEDs within dark field illumination unit 400 may be activated and/or adjusted.

A pivoting structure 630, as previously described in connection with FIG. 3A, is shown coupled to a reflector unit 100 which is positioned above table 350. In FIG. 4A reflector unit 100 is shown in its down position, in registration with base unit 300 and dark field illumination unit 400.

Also shown in FIG. 4A is a lens 356 and imaging device 358 supported above and in registration with reflector unit 100. Imaging device 358 is shown electrically coupled to imaging device control 362, which communicates with computer 364. With such a configuration, a user is able to control imaging device 358 to view, capture, and store images of the gem under inspection, and to further process the captured images, such as in a clarity grading operation.

The imaging device 358 is supported by an imaging device mount 360, which, in turn, is supported by post 366. Post 366 is coupled to and supported by table 350. An enlarged view of imaging device mount 360 and post 366 is provided in FIG. 4B. Preferably, imaging device mount 360 provides an X-Y-Z positioning capability, so that imaging device 358 and lens 356 may be positioned in X, Y and Z directions with respect to the table 350, and to a gem under inspection that may be positioned within reflector unit 100 and supported by the table 350.

Preferably imaging device mount 360 includes three rack and pinion arrangements by which X, Y, and Z positions of imaging device 358 may be adjusted. In FIG. 4B, mounting screw 368 is shown, for coupling imaging device 358 to imaging device mount 360. In turn, mounting screw 368 is coupled to Z-axis rack 370 which is a part of a Z-axis rack and pinion assembly 372 that provides a Z-axis positioning capability. Z-axis rack and pinion assembly 372, in turn, is coupled to X-axis rack and pinion assembly 374 that provides an X-axis positioning capability. The X-axis pinion 376 of X-axis rack and pinion assembly 374 is coupled to the Y-axis pinion 378 of Y-axis rack and pinion assembly 380 that provides a Y-axis positioning capability.

In the embodiment of FIG. 4B, an "L" shaped bracket is employed to couple the X, Y and Z rack and pinion assemblies to a linear translation stage referred to as vertical position rack and pinion assembly 382. This latter assembly permits the vertical positioning of the lens 356, imaging device 358 and imaging device mount 360 with respect to table 350, and the gem under inspection. Vertical position rack 384 of vertical position rack and pinion assembly 382 is shown coupled to post 366. Post 366 is secured to table 350 using brackets 386 and/or other suitable fastening mechanisms.

In the preferred embodiment of the configurations of FIGS. 4A, and 4B, the X-Y-Z moving stage of the imaging device mount 360 may be XYZ stage model number T55-621, manufactured by Edmund Optics Ltd., Tudor House, Lysander Close, Clifton Moor, York Y030 XB England. The linear translation stage of vertical position rack and pinion 382 may be linear translation stage 125 mm model T56-794/5, also manufactured by Edmund Optics Ltd.

The efficacy of the present invention was researched using various cameras. A brief discussion of this experimentation is provided below.

First, with respect to a conventional Nikon FE camera, it was discovered that obtaining digital images required getting the slide film developed and then scanned with a professional digital scanner. These steps were time consuming and cumbersome, and they hindered further development of the application. A professional digital camera has no such disadvantages, but only high-end digital photographical equipment can compete with the resolution of the images obtained by scanning traditional slides.

Several other digital cameras were tested as they became available. The Nikon D1, for example, offered higher quality results than many others in part because of the high quality lenses available for that camera. The Nikon D1 digital camera comes with Nikon Capture software allowing camera settings and shutter release from a computer keyboard. The software captures and stores the images as thumbnails which can be enlarged and then saved in a digital archive. Data transfer between the computer and the camera is done by FireWire communication protocol, also known as the IEEE 1394a data transfer standard, which requires a special Fire Wire card to be installed in the computer.

Many of the camera settings were tested in order to find the best possible settings for acquiring diamond images. The most important adjustable camera settings include diaphragm pre-settings, magnification, light metering and correction methods, focusing field choices, image quality and image storage possibilities, white balance options and shutter speed settings. The most appropriate lens proved to be 60 mm f/2.8D which had a high depth of field (the depth of field is depending on the chosen diaphragm and the magnification). With the 60 mm lens, a maximum depth of field range of about 5 mm can be obtained at the required 2× magnification. This range is sufficient to have a 1 ct stone in full focus between table and culet.

For larger diameter diamonds, the magnification should be adjusted in order to have a complete image of the stone, but the depth of field will also increase which will help. To obtain a magnification range of at least 2×, a set of extension rings (Nikon PK11+12+13) should be mounted in between the camera body and the 60 mm lens.

In an alternative embodiment, a real time camera may be used, such as a model MegaPlus ES-4020, manufactured by Redlake Inc./IDT of Tallahassee, Fla. The imaging device control 362 employed with the Nikon D1 or the Redlake/IDT MegaPlus ES-4020 are the standard interface units commercially available for these imaging devices, such as a head controller unit with CameraLink or FireWire output, and control software, that accompanies the Redlake/IDT model MegaPlus ES-4020.

The preferred hardware setup between computer and camera involves a camera that acquires images only when the keyboard is touched. This means that the proper orientation of the diamonds can only be checked after the image is shot. A real time camera, however, may be employed to acquire images continuously while the diamond is being oriented, allowing the process of setting-up to take much less time because the image can be checked continuously for better optimization of the image.

In the discussion that follows, schematics detailing the structural dimensions of various aspects of the present invention are provided, wherein dimensions for a particular embodiment are given. Here, it should be noted that such dimensions are provided solely as an example of a particular embodiment and are not intended to limit the scope and spirit of the invention. Furthermore, it will be apparent to one skilled in the art upon reading the these descriptions that other materials, configurations and arrangements can be used to implement the teachings of this application and the concepts of the present invention.

Figure 5A:
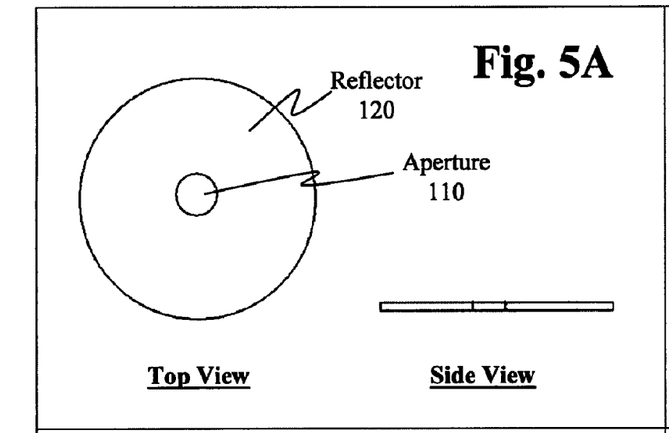
FIG. 5A is a structural schematic of the reflector and aperture of a reflector unit according to an embodiment of the invention.

In FIGS. 5A-5D, schematics detailing the structural dimensions for reflector unit 100, according to a preferred embodiment, are provided. In FIG. 5A, for example, a schematic of aperture 110 and reflector 120 is provided. For this particular embodiment, reflector 120 is an aluminum reflector having a thickness of approximately 2 millimeters (mm) and a diameter of approximately 60 mm. Aperture 110 may have a diameter of approximately 14 mm to 20 mm. Reflector 120 may be constructed of AlMgSi 0.5 F22—half hardness—aluminum alloy. The surface of reflector which faces the interior of reflector unit 100 is preferably highly polished or chrome plated.

Figure 5B:
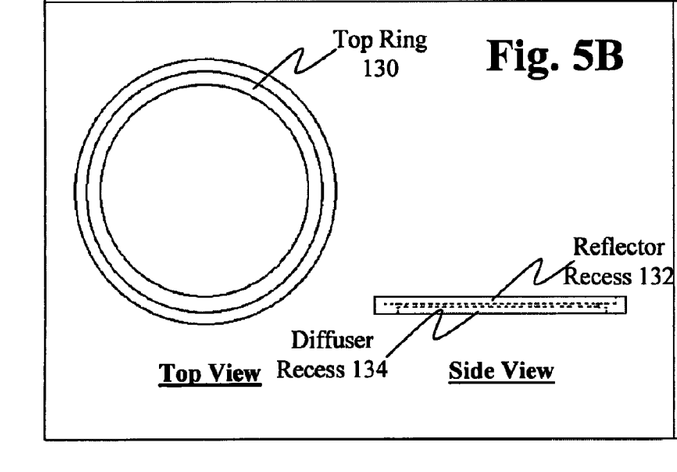
FIG. 5B is a structural schematic of the top ring of a reflector unit according to an embodiment of the invention.

In FIG. 5B, a schematic of top ring 130 is provided. For this particular embodiment, top ring 130 is a black nylon ring having a thickness of approximately 6 mm, and outer diameter of approximately 68.5 mm, and an inner diameter of approximately 49 mm. As illustrated, top ring 130 has a reflector recess 132 of approximately 60.5 mm in diameter for supporting reflector 120, and a diffuser recess 134 of approximately 55.6 mm in diameter for engaging diffuser glass 140.

Figure 5C:
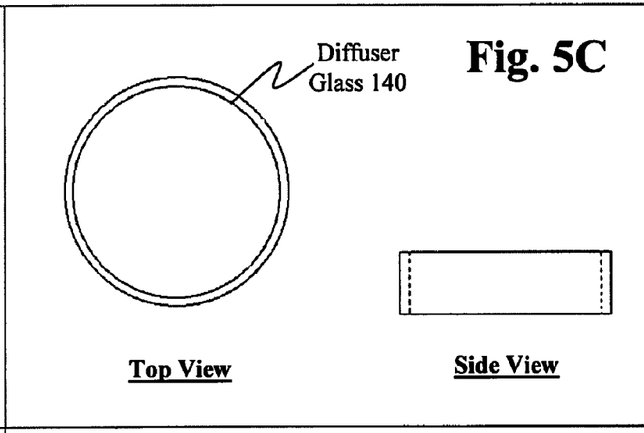
FIG. 5C is a structural schematic of the diffuser glass of a reflector unit according to an embodiment of the invention.

In FIG. 5C, a schematic of diffuser glass 140 is provided. For this particular embodiment, diffuser glass 140 has a height of approximately 19 mm, a glass thickness of approximately 4 mm, and a diameter of approximately 55.5 mm. Diffuser glass 140 may be constructed of boron silicate glass, such as that sold under the mark PYREX®, a registered trademark of Corning Incorporated, Corning, N.Y., or other very strong and hardened laboratory glass type. Surface treatment is preferably pearl blasting using 125 micron dry pearls. The diffuser portion of rotating diffuser unit 230 may also be constructed of such processed boron silicate glass.

Figure 5D:
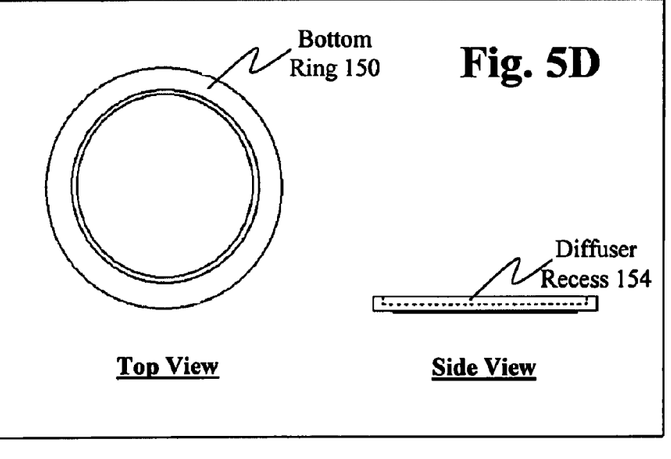
FIG. 5D is a structural schematic of the bottom ring of a reflector unit according to an embodiment of the invention.

In FIG. 5D, a schematic of bottom ring 150 is provided. For this particular embodiment, bottom ring 150 is formed preferably of black nylon and has a total height of approximately 4 mm, an outer diameter of approximately 70 mm, and an inner diameter of approximately 48.5 mm. As illustrated, top ring 130 also includes a diffuser glass recess 154, which has a diameter of approximately 55.6 mm for accommodating diffuser glass 140. The 4 mm height of bottom ring 150 includes a body portion of approximately 3 mm and an extension portion of approximately 1 mm. The extension portion of bottom ring 150 is sized to accommodate bottom plate 210 of base unit 200.

Figure 6A:
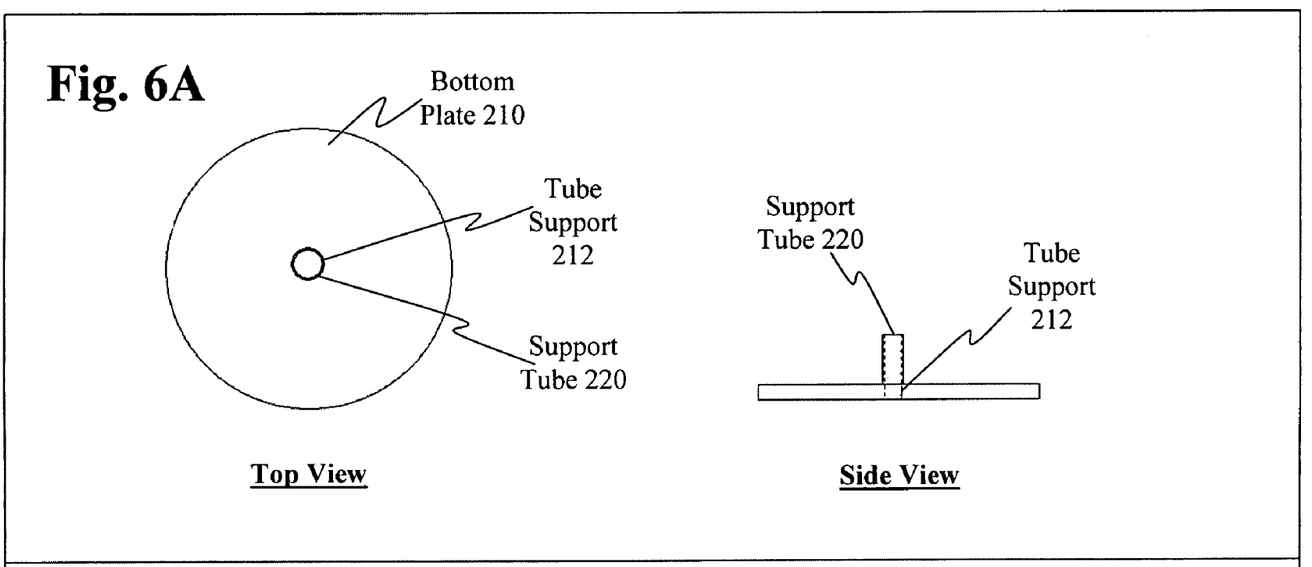
FIG. 6A is a structural schematic of the bottom plate of a base unit according to an embodiment of the invention.
Figure 6B:
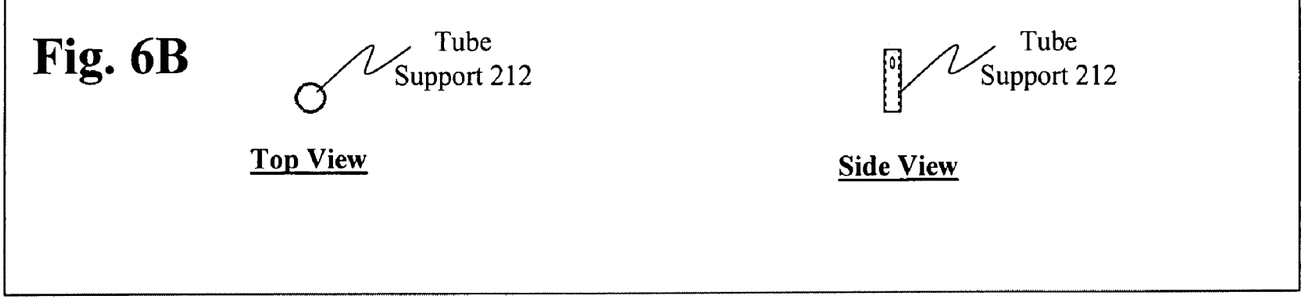
FIG. 6B is a structural schematic of the support tube of a base unit according to an embodiment of the invention.

In FIGS. 6A-6B, schematics detailing the structural dimensions for base unit 200, according to a preferred embodiment, are provided. In FIG. 6A, for example, a schematic of bottom plate 210 is provided, wherein bottom plate 210 is shown to further include support tube 220 and tube support 212. For this particular embodiment, bottom plate 210 is preferably formed of white TEFLON®, more specifically natural TEFLON® Ertafluor PTFE for its white and diffuse character. Bottom plate preferably has a thickness of approximately 3 mm, and a outer diameter of approximately 48 mm. Meanwhile, support tube 220 has a height of approximately 12 mm, and an outer diameter of approximately 5 mm at the top and an inner diameter of approximately 4 mm. Support tube 220 may include prongs (not shown) for accommodating a gem, such as a diamond. The prongs are preferably splayed slightly outward in order to permit the gem to be more easily placed on the support tube.

In FIG. 6B, a schematic of tube support 212 is provided. For this particular embodiment, tube support 212 has a height of approximately 20 mm, an outer diameter of approximately 4 mm, and an inner diameter of approximately 3 mm so as to allow support tube 220 to be placed coaxially over tube support 212. From FIG. 6A, it can be seen that bottom plate 210 has a center aperture, which in this embodiment is approximately 4 mm in diameter, to permit one end of tube support 212 to pass there through to the opposite side. A well-guard situated proximate to support tube 220 may also be used so as to mitigate the possible loss of a gem. Support tube 220 may be fabricated out of stainless steel, for example.

Figure 7A:
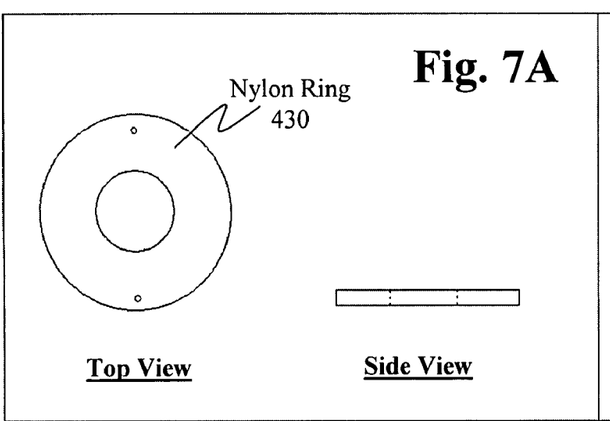
FIG. 7A is a structural schematic of the nylon ring of an illumination unit according to an embodiment of the invention.
Figure 7B:
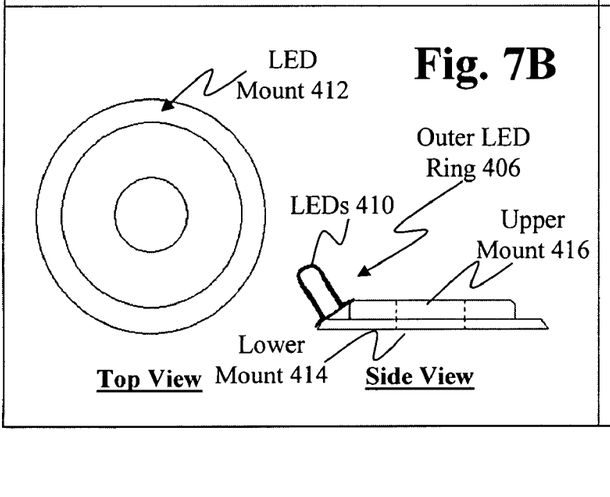
FIG. 7B is a structural schematic of the LED mount of an illumination unit according to an embodiment of the invention.
Figure 7C:
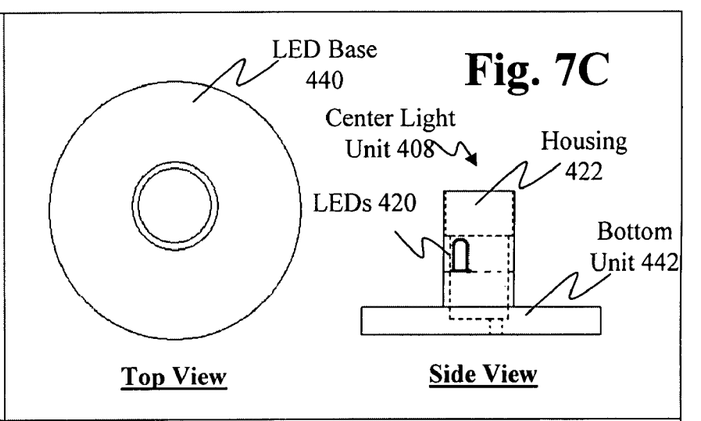
FIG. 7C is a structural schematic of the LED base of an illumination unit according to an embodiment of the invention.

In FIGS. 7A-7D, schematics detailing the structural dimensions for dark field illumination unit 400, according to a preferred embodiment, are provided. Dark field illumination unit 400 includes a base 440 which supports a ring of LEDs 410 to form outer LED ring 406, and an inner group of LEDs 420 positioned in a center light unit 408. In FIG. 7A, for example, a schematic of ring 430 is provided. For this particular embodiment, ring 430 is a ring preferably formed of white nylon and having a thickness of approximately 5 mm, an outer diameter of approximately 40 mm, and an inner diameter of approximately 25 mm. Ring 430 is positioned over LED mount 412 (FIG. 7B), which in turn is positioned over bottom unit 442 of LED base 440 (FIG. 7C). LEDs preferably have a typical luminous intensity of 200 mcd, or better, such as those manufactured by Nichia Corporation, Tokyo, Japan. The LEDs may have an opening angle of approximately 20% and a color temperature of approximately 5500 degrees Kelvin. It is believed that newer LEDs which are becoming available, such as those with 50% degree opening angles, may be employed in the present invention to further improve the performance of the invention.

In FIG. 7B, a schematic of LED mount 412 is provided, wherein LED mount 412 is preferably formed of white nylon and includes a ring of LEDs 410. Mounting base 412 is preferably white so that no additional color is introduced, and is preferably formed of an insulating material, such as nylon, in order to provide electrical isolation for LEDs 410. LEDs 410 are mounted onto lower mount 414 and upper mount 416, as shown, so as to be angled outwardly from the center axis of LED mount 412. For this particular embodiment, lower mount 414 has a thickness of approximately 2 mm, an outer diameter of approximately 50 mm, and an inner diameter of approximately 25 mm. Meanwhile, upper mount 416 has a thickness of approximately 4.8 mm, an outer diameter of approximately 45 mm, and an inner diameter of approximately 25 mm. For this embodiment, it should also be appreciated that the outer LED ring 406 preferably includes a total of 24 individual LED units.

In FIG. 7C, a schematic of LED base 440 is provided, wherein LED base 440 is preferably composed of aluminum and includes inner LEDs 420 housed within housing 422, which, in turn, is mounted onto bottom unit 442, as shown. For this particular embodiment, bottom unit 442 has a thickness of approximately 7.5 mm, and outer diameter of approximately 62 mm, and a support ring recess formed to accommodate support ring 460. Meanwhile, housing 422 has a height of approximately 32.5 mm, an outer diameter of approximately 26 mm, and an inner diameter of approximately 18 mm. At the top of housing 422 is formed a recess of approximately 21 mm in diameter. For this embodiment, it should also be appreciated that inner LEDs 420 preferably include a total of 6 individual LED units which are aligned to be substantially parallel with the center axis of LED base 440.

Figure 7D:
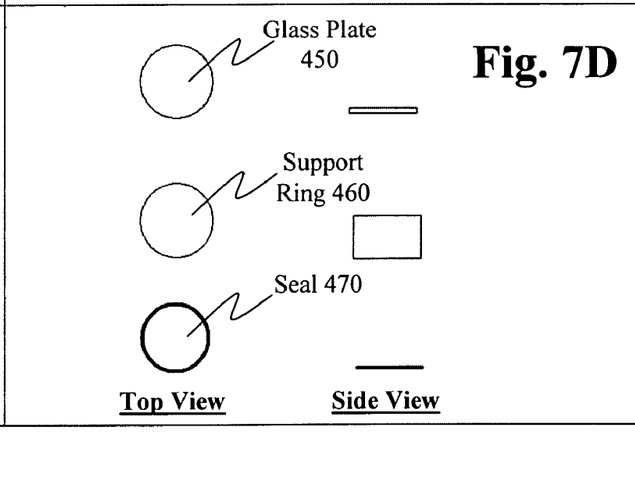
FIG. 7D is a structural schematic of the glass plate, support ring, and seal of an illumination unit according to an embodiment of the invention.

In FIG. 7D, a schematic of plate 450, support ring 460, and seal 470 is provided. For this particular embodiment, plate 450 is a glass plate having a thickness of approximately 1.6 mm and a diameter of approximately 21 mm; support ring 460 is preferably formed of white nylon and has a height of approximately 19.6 mm and a diameter of approximately 18 mm; and seal 470 is a rubber seal having a thickness of approximately 1.5 mm and a diameter of approximately 22 mm. One end of support ring 460 is positioned in the support ring recess in bottom unit 442 of LED base 440. Housing 422 fits over support ring 460, and inner LEDs 420 are positioned within support ring 460. Glass plate 450 is positioned in housing 422 on top of support ring 460 and over inner LEDs 420.

Figure 8A:
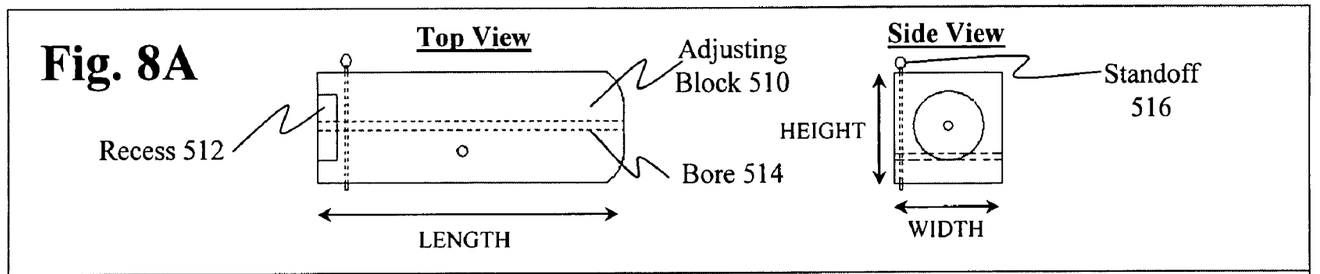
FIG. 8A is a structural schematic of the adjusting block of a camera mounting unit of FIG. 3B according to an embodiment of the invention.
Figure 8B:
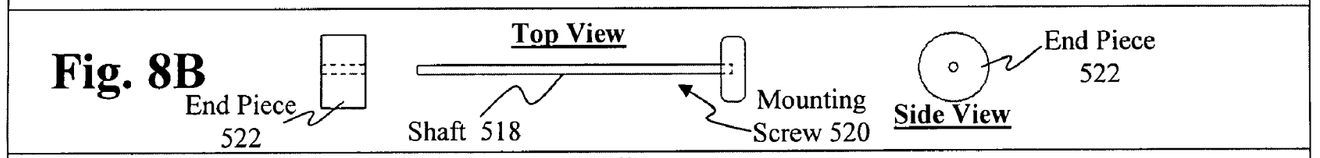
FIG. 8B is a structural schematic of the mounting screw of a camera mounting unit of FIG. 3B according to an embodiment of the invention.
Figure 8C:
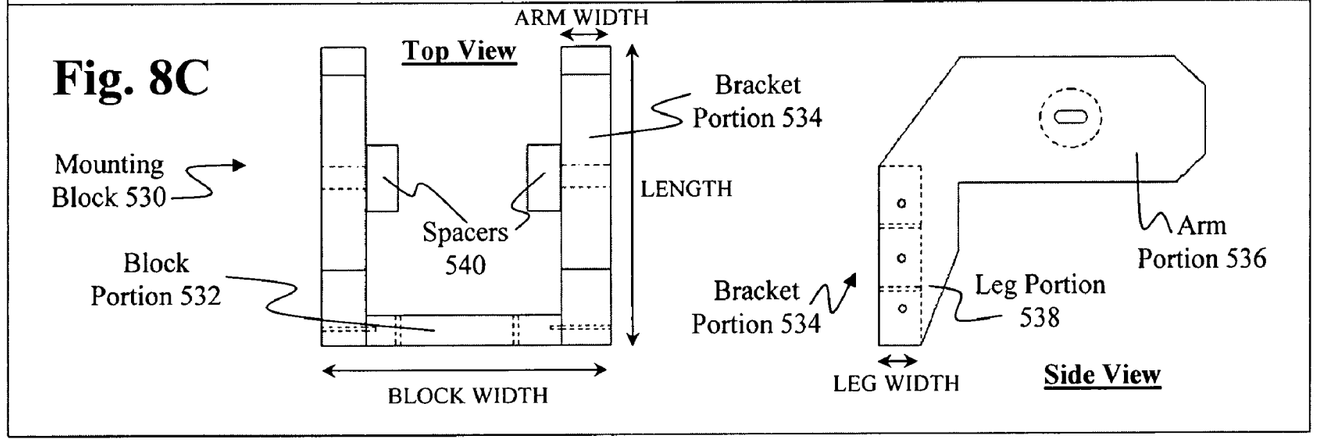
FIG. 8C is a structural schematic of the mounting block of a camera mounting unit of FIG. 3B according to an embodiment of the invention.

In FIGS. 8A-8C, schematics are provided detailing the structural dimensions for camera mounting unit 500, according to an embodiment in which a camera remains in a fixed position with respect to a moveable a stage that supports the reflector unit 100 and base unit 200. FIG. 3B illustrates the camera mounting unit, as assembled. Camera mounting unit 500 is preferably used to mount a camera in place of the tube of a microscope, so that the camera lens axis is centered in the microscope's illumination set up. The reflected dark field unit of the present invention would then be positioned on or as the stage of the microscope and aligned to be centered with the camera lens axis.

In FIG. 8A, for example, a schematic of adjusting block 510 is provided. For this particular embodiment, adjusting block 510 is preferably formed of aluminum and has a height of approximately 40 mm, a width of approximately 40 mm, a length of approximately 100 mm. Adjusting block 510 includes a recess 512 at one end which has a diameter of approximately 28 mm, and a bore 514 which extends from recess 512 to the opposite end of the adjusting block 510. The recess 512 is sized to accommodate end piece 522 of mounting screw 520, and bore 514 is configured to accommodate the shaft 518 of mounting screw 520. An adjustable standoff 516 is also shown in FIG. 8A, positioned to one side of recess 512. Adjustable standoff 516 can be used to provide a hard stop for the adjusting block 510 at a selectable distance relative to the mounting block 530.

In FIG. 8B, a schematic of camera mounting screw 520 is provided. For this particular embodiment, camera mounting screw 520 has a length of approximately 95 mm and a diameter of approximately 20 mm. The shaft 518 of mounting screw 520 is configured to extend through bore 514 of adjusting block 510 into recess 512, and end piece 522 to then couple to the end piece 522. End piece 522 and the end of shaft 518 are suitably configured to permit mounting of a camera body to adjusting block 510.

In FIG. 8C, a schematic of mounting block 530 is provided. For this particular embodiment, mounting block 530 is preferably formed of aluminum and includes a block portion 532 which joins two bracket portions 534 together. Each bracket portion 534 has an arm portion 536, a leg portion 538, and a spacer 540. Arm portion 536 has length of approximately 120 mm, an arm width of approximately 10 mm. Leg portion 538 has a leg width of approximately 20 mm. Block portion 532 has a block width of approximately 70 mm. FIG. 8C illustrates a side view of leg portion 538 and, in phantom, shows the orientation of block portion 532 with respect to leg portion 538.

As can be seen in FIG. 3B, adjusting block 510 is pivotally coupled to arm portion 536 of mounting block 530, by way of spacers 540 and an adjusting screw 542. Adjusting screw 542 has a shaft which extends through bores formed in spacers 540, in adjusting block 510, and in arm portions 536. Adjusting screw 542 is suitably configured to cause bracket portions 534 to apply pressure to adjusting block 510 by way of spacers 540, to thereby fix adjusting block in a desired position relative to mounting block 530. In FIG. 8C, several bores are shown formed in block portion 532 through which camera mounting unit 500 may be suitably attached to a microscope arm by screws or other suitable fasteners. In practice, a rack and pinion or other positioning structure of the microscope is abutted against the inside surface of block portion 532, and between leg portions 538. Set screws or other suitable fasteners can then be inserted through the bores of block portion 532 to secure the camera mounting unit 500 to the microscope positioning structure.

Preferably, the following materials are employed for the aluminum, TEFLON®, Glass, and black plastic parts in the embodiments described above. For the aluminum parts: aluminum alloy AlMgSi 0.5 F22—half hardness, an alloy that is easy to machine; surface treatment of a black coating of 15 micron thickness or high finish polishing. TEFLON® parts: natural TEFLON® Ertafluor PTFE, which has a white and diffuse character. Glass parts: boron silicate glass, sold under the mark PYREX®, a registered trademark of Corning Incorporated, which is a very strong and hardened laboratory glass type; surface treatment pearl blasting 125 micron dry pearls. Black Plastic parts: Ertacetal black POM-C, sometimes referred to by the mark DELRIN a registered trademark of E. I. du Pont de Nemours and Company, Corp. of Wilmington Del., a material which has easy machining properties.

The present invention has been described above with reference to several different embodiments. However, those skilled in the art will recognize that changes and modifications may be made in the above described embodiments without departing from the scope and spirit of the invention. Furthermore, while the present invention has been described in connection with a specific processing flow, those skilled in the art will recognize that a large amount of variation in configuring the processing tasks and in sequencing the processing tasks may be directed to accomplishing substantially the same functions as are described herein. These and other changes and modifications which are obvious to those skilled in the art in view of what has been described herein are intended to be included within the scope of the present invention.

What is claimed is:

1. A dark field illumination apparatus comprising:
   a base plate;
   a support tube positioned on the base plate and having an end configured to support a gem;
   a diffuser structure configured to substantially encircle the gem supported by the support tube;
   a reflector unit having a reflecting surface positionable over the diffuser structure and to be opposite the surface of the base plate so that the gem supported by the support tube is substantially surrounded by the reflecting surface, the diffuser structure and the base plate, wherein the reflector unit includes an aperture formed in the reflecting surface to allow the gem supported by the support tube to be viewed; and
   a light unit positioned to illuminate the gem supported by the support tube and so that the gem supported by the support tube is located between the light unit and the reflecting surface;
   wherein the base plate comprises a material through which light can pass, and the light unit is positioned so that the base plate is located between the light unit and the gem supported by the support tube.

2. The dark field illumination apparatus of claim 1, wherein the base plate includes a neutral density filter.

3. A dark field illumination apparatus comprising:
   a base plate;
   a support tube positioned on the base plate and having an end configured to support a gem;
   a diffuser structure configured to substantially encircle the gem supported by the support tube;
   a reflector unit having a reflecting surface positionable over the diffuser structure and to be opposite the surface of the base plate so that the gem supported by the support tube is substantially surrounded by the reflecting surface, the diffuser structure and the base plate, wherein the reflector unit includes an aperture formed in the reflecting surface to allow the gem supported by the support tube to be viewed; and
   a light unit positioned to illuminate the gem supported by the support tube and so that the gem supported by the support tube is located between the light unit and the reflecting surface;
   wherein the support tube is configured to permit passage of direct illumination from the light unit through the support tube to the gem supported by the support tube.

4. A dark field illumination apparatus comprising:
   a base unit;
   a support tube affixed onto the base unit and configured to hold a gem;
   a diffuser structure formed of glass and configured to provide a perimeter around the gem held by the support tube;
   a top reflector unit positioned on the diffuser structure to provide a top cover for the gem held by the support tube, wherein the top reflector unit includes a reflecting surface and the reflecting surface includes an aperture configured to allow the gem held by the support tube to be viewed; and
   a light unit coupled to the base unit, wherein the light unit and the base unit are configured so that the gem held by the support tube is illuminated directly by light from the light unit passing through the base unit and indirectly by light reflected from the top reflector unit.

5. The dark field illumination apparatus of claim 4, further including an imaging device positioned to image the gem held by the support tube, wherein the imaging device is coupled to the base by a stage that is adjustable in X, Y and Z directions.

6. The dark field illumination apparatus of claim 4, wherein the support tube is dimensioned so that the base unit is beyond a field of view of a camera which is positioned to image a gemstone held by the support tube.

7. The dark field illumination apparatus of claim 4 further comprising a well guard.

8. The dark field illumination apparatus of claim 4, wherein the support tube further includes prongs oriented outwardly and configured to engage the gem supported by the support tube.

9. The dark field illumination apparatus of claim 4, wherein a path between the gem and the aperture along a longitudinal axis of the support tube is unobstructed.

* * * * *